United States Patent [19]

Nitta et al.

[11] 4,080,564

[45] Mar. 21, 1978

[54] HUMIDITY SENSITIVE RESISTOR DEVICE

[75] Inventors: Tsuneharu Nitta, Katano; Ziro Terada, Yao; Shigeru Hayakawa, Hirakata, all of Japan

[73] Assignee: Matsushita Electric Industrial Co., Ltd., Kadoma, Japan

[21] Appl. No.: 727,380

[22] Filed: Sep. 27, 1976

[30] Foreign Application Priority Data

Oct. 2, 1975 Japan .............................. 50-119524
Jan. 20, 1976 Japan ................................. 51-5621

[51] Int. Cl.$^2$ ........................................... G01R 27/02
[52] U.S. Cl. .................................... 324/65 R; 73/73; 219/10.55 B; 338/35
[58] Field of Search .............. 324/65 R, 65 P; 338/35; 73/73; 219/10.55 B

[56] References Cited

U.S. PATENT DOCUMENTS

| | | | |
|---|---|---|---|
| 3,047,801 | 7/1962 | Dietert | 324/65 R X |
| 3,234,458 | 2/1966 | Bean et al. | 324/65 P |
| 3,367,185 | 2/1968 | Wakefield | 324/65 R X |
| 3,958,176 | 5/1976 | Kraeutle | 324/65 R |
| 4,011,538 | 3/1977 | Froemel | 338/35 |
| 4,015,230 | 3/1977 | Nitta et al. | 338/35 |

FOREIGN PATENT DOCUMENTS 1,259,566  2/1972  United Kingdom .............. 324/65 R

*Primary Examiner*—Stanley T. Krawczewicz
*Attorney, Agent, or Firm*—Wenderoth, Lind & Ponack

[57] ABSTRACT

A humidity sensitive resistor device for sensing the humidity of an ambient atmosphere. The device has a humidity sensitive resistor formed by a metal oxide sintered substrate having electrodes on one surface thereof, the resistivity of the humidity sensitive resistor decreasing as the ambient humidity which can affect the surface of the humidity sensitive resistor increases; and a heater positioned near the humidity sensitive resistor for applying radiant heat to the surface of the humidity sensitive resistor, which heater can be used for improving the sensitivity of the humidity sensitive resistor. By the application of a slight amount of radiant heat, the humidity sensitivity increases, and by the application of a large amount of strong heat, stains which may be on the surface of the humidity sensitive resistor such as oil can be cleaned off so as to recover the sensitivity of the humidity sensitive resistor which might have been deteriorated by the stain.

10 Claims, 7 Drawing Figures

HUMIDITY SENSITIVE RESISTOR DEVICE

This invention relates to a humidity sensitive resistor device, and more particularly to a novel humidity sensitive resistor device comprising a metal oxide sintered substrate having electrodes deposited on one surface thereof and a heater provided around the substrate.

Recently, a microwave oven, an electronic oven, etc. using a humidity sensitive resistor have been developed for the purpose of cooking food by a heating procedure. A conventional humidity sensitive resistor comprises a substrate having humidity activity and electrodes deposited on the substrate. When the foods are heated for cooking, they eject a humid vapor. It is well known that the foods can be cooked by controlling the cooking temperature in response to the humidity of the vapor. However, the cooking controlling method encounters two main problems: (1) Since the temperature as well as the relative humidity in these ovens are changed with a change of time, day, season and/or the number of times cooking has been carried out, the cooking by such appliances using a conventional humidity sensitive resistor cannot be performed consistently; and (2) Since the foods eject not only humid vapor, but also oil vapor and other organic vapors during heating and cooking, the sensitivity of the humidity sensitive resistor is reduced thereby.

Accordingly, a principal object of this invention is to provide a humidity sensitive resistor device which can retain its high humidity sensitivity.

Another object of this invention is to provide a humidity sensitive resistor device which can respond constantly to the change of the ambient humidity despite the fluctuation of the initial humidity before the humidity change.

Yet another object of this invention is to provide a humidity sensitive resistor device which can recover, by itself, from possible deterioration of its humidity sensitivity due e.g. to oil deposited on the working surface of the humidity sensitive resistor.

These objects are achieved according to this invention by a humidity sensitive resistor device comprising: a humidity sensitive resistor formed by a metal oxide sintered substrate having electrodes on one surface thereof, the resistivity of the humidity sensitive resistor decreasing as the ambient humidity increases; and a heater positioned near the humidity sensitive resistor for applying radiant heat to the working surface of the humidity sensitive resistor, wherein the radiant heat in a small amount can be used for keeping constant the surface moisture condition of the humidity sensitive resistor, and the radiant heat in a large amount can be used for removing or cleaning off stains such as oil which may have been deposited on the working surface of the humidity sensitive resistor.

These and other objects and features of this invention will better be understood from the following detailed description in conjunction with the accompanying drawings, in which.

Figure 1:
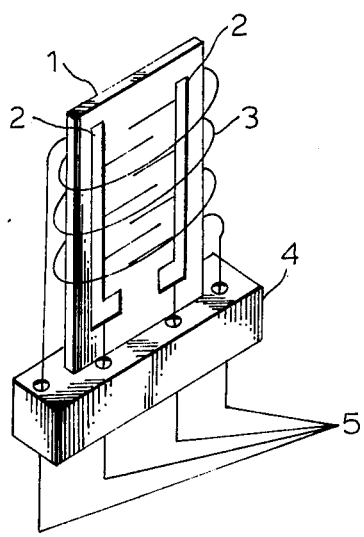
FIG. 1 is a perspective view of a preferred embodiment of a humidity sensitive resistor device according to this invention.

Referring to FIG. 1, there is shown, in a perspective view, the basic structural features of a humidity sensitive resistor device according to one embodiment of this invention. The humidity sensitive resistor device shown basically comprises a metal oxide sintered substrate 1 having a humidity sensitive characteristic and interdigital electrodes 2 deposited on one surface of the sintered oxide. A wire heater 3 is positioned near the substrate. These elements are supported by a shoe substrate 4 through which lead-wires 5 are passed to be connected to a heater. The sintered substrate consists essentially of a metal oxide and has a humidity sensitive property in a lower temperature range and a NTC thermistor property in a higher temperature range. Most of the known metal oxides have a humidity sensitive characteristic as a well as NTC thermistor one.

A preferred metal oxide for the sintered substrate 1 is taken from the group consisting of $Cr_2O_3$, $Fe_2O_3$, NiO, ZnO, $SnO_2$, $TiO_2$, $Al_2O_3$, MgO, $In_2O_3$, $MnO_2$, CuO, CoO, $MgCr_2O_4$, $FeCr_2O_4$, $NiCr_2O_4$, $MnCr_2O_4$, $CuCr_2O_4$, $CoCr_2O_4$, $Zn_2TiO_4$, $Zn_2SnO_4$, $Mg_2TiO_4$ and $Mg_2SnO_4$. The best metal oxide sintered substrate 1 comprises as a main component a material taken from the group consisting of $Cr_2O_3$ and $MgCr_2O_4$.

The metal oxide sintered substrate used in this invention can be prepared by a per se well known fabrication method. The component oxide powders are intimately mixed with water in the desired composition proportions and then dried. The dried powder is admixed with an organic binder. The thus prepared powder mixture is then pressed into a plate form. The plate is sintered at a high temperature of 1100° C to 1600° C. By the sintering, the organic binder is evaporated.

The interdigital electrodes 2 can also be formed in a per se conventional manner. Preferable materials for the electrode are Ag, Au, Ag-Pd alloy, Ni-P alloy, Pt, $RuO_2$, NiO, $SnO_2$, $In_2O_3$, $TiO_2$, ZnO, $BaTiO_3$ and $BaPbO_3$, which are conductive materials characterized by having a lower electrical resistance than that of the metal oxide sintered substrate. Among these electrodes, $RuO_2$, $SnO_2$ and $In_2O_3$ produce the best results.

Then the heating element 3 can be positioned around the electrode containing sintered substrate. For the heater 3 there can be used any suitable material such as a metal wire of Ni-Cr alloy (Nichrom), Ni-Cr-Al alloy (Kantal), Fe-Cr alloy, Ni-Al (Alumel) and Pt.

A preferred embodiment is given described below. A sintered substrate for the humidity sensitive resistor device is made in a per se conventional manner. The raw materials used are commercially pure grade MgO, $Cr_2O_3$ and $TiO_2$. The composition ratio is 80 mole MgO, 80 mole $Cr_2O_3$ and 20 mole $TiO_2$. A batch of raw materials is ball-milled with water for intimate mixing and then is dried. The powder is admixed with an emulsion of polyvinyl alcohol in a proportion of 100 grams of the powder to 12 cc of a 6 percent aqueous emulsion of polyvinyl alcohol. The powder mixture is then pressed at 750 kg/cm² into a rectangular plate 6 mm × 3 mm and 0.15 mm in thickness. The plate is sintered in air at 130° C for one hour, while supported on an alumina plate. The sintered plate is polished by a per se well known method, resulting in a finished thickness of 0.10 mm. The polished plate is then provided on one surface with interdigital electrodes. Ruthenium oxide paste is fired at 800° C on the plate surface to form the electrodes in a per se conventional manner.

As a heater there is used a Kantal wire 0.15 mm in diameter. The heater, which is constructed in a spriral or wave form, is bonded to a shoe substrate, for example, alumina ceramic, together with the metal oxide sintered substrate having the electrodes deposited thereon by a per se conventional method, for example, spot-welder bonding.

Then the humidity property and NTC thermistor characteristic are measured by a per se well known method for the thus made humidity sensitive resistor device. Electrical resistance is measured by applying a field of 1 V(A.C.). Humidity activity is obtained by measuring electrical resistance in a range of relative humidity of 0% to 100% at 20° C. Temperature-dependence of electrical resistance is measured in a range of temperature of 0° C to 600° C.

Figure 2:
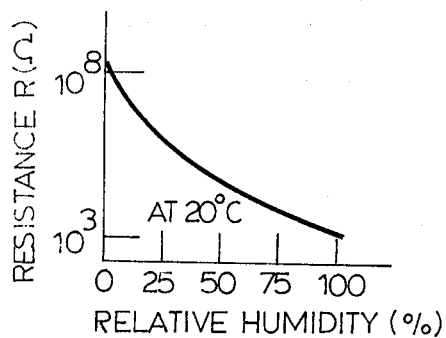
FIG. 2 is a graph illustrating the relation between the electrical resistance and relative humidity of an example of a humidity sensitive resistor used in this invention.

The measured humidity property of the thus formed humidity sensitive resistor device is shown in FIG. 2. As is apparent from FIG. 2, the metal oxide sintered substrate results in a high humidity activity.

Figure 3:
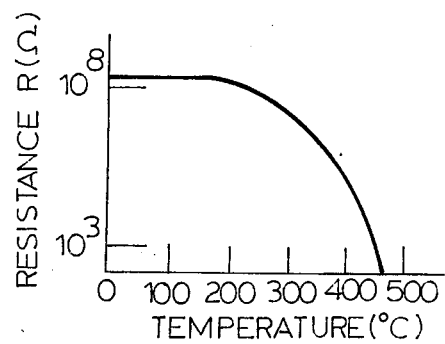
FIG. 3 is a graph illustrating the relation between the electrical resistance and temperature of the humidity sensitive resistor used in making the graph of FIG. 2.

The thermistor property of the metal oxide sintered substrate is shown in FIG. 3. As shown in FIG. 3, the humidity sensitive metal oxide sintered substrate has a characteristic for temperature vs. the logarithmic value of electrical resistance which is nearly linear in a range of temperature of about 150° C to 500° C.

One of the advantages of the humidity sensitive resistor is that the temperature range of the humidity sensitive property does not overlap the temperature range of the NTC thermistor property. That is, at the lower limit temperature of the NTC thermistor region, e.g. 150° C, the humidity sensitive resistor does not have a humidity sensitive property because moisture is unlikely to be adsorbed on the surface of the humidity sensitivity resistor at such a high temperature. One example of the way of using the NTC thermistor property will be described later. Advantages of using a sintered material are that powders can be sintered into any desired shape and it can be produced by mass production, and that the sintered material is highly resistant to thermal shock, oxidation and reduction.

Now when the humidity sensitive resistor device is used for the above-described food cooking which is carried out by controlling the cooking temperature in response to the humidity of the vapor ejected from the foods during the heating e.g. in a microwave oven, the heater arrangement can advantageously be used as will be described below.

Figure 4A:
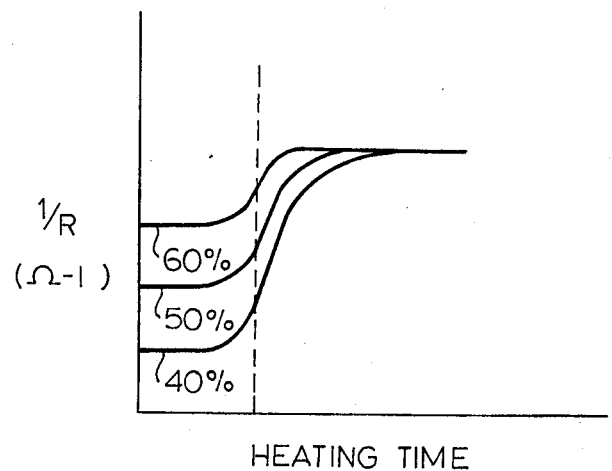
FIG. 4 is a graph illustrating the change of relative humidity with heating time when water is heated in a micro-wave oven, in which the parameter is the initial relative humidity in the oven before heating; (a) using a conventional humidity sensitive resistor device, and (b) using a humidity sensitive resistor device according to one example of this invention.
Figure 4B:
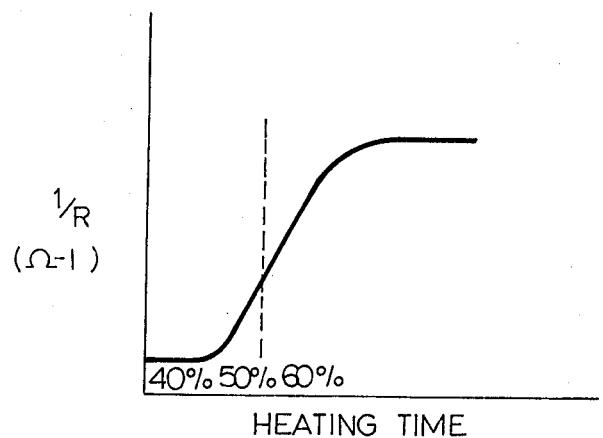

Referring now to FIGS. 4(a) and 4(b), there are shown graphs illustrating the change of relative humidity with heating time when water is heated by microwaves in a microwave oven, in which the variable parameter is the initial relative humidity in the oven before heating. FIG. 4(a) is a graph for the case of a conventional humidity sensitive resistor device. As is apparent from FIG. 4(a), with the conventional humidity sensitive resistor device, the humidity sensitive resistor has three different resistances in accordance with the three different initial humidities, 40%, 50% and 60%, for the same heating time (e.g. the dottod line) by the microwaves. This means that if the conventional humidity sensitive resistor device is used in a microwave oven to switch off the microwave oven just after the desired heating time, the switch-off timing is not constant due to the fluctuation of the initial humidity (before the start of cooking), and thus a desired cooking time cannot be well controlled.

FIG. 4(b) is a graph for the case when the heater in the humidity sensitive resistor device according to this invention is heated to apply radiant heat to the humidity sensitive resistor by using a control arrangement, as shown e.g. in FIG. 5 (described later), included in the humidity sensitive resistor device. As is apparent from FIG. 4(b), the heater arrangement of the device according to this invention can achieve pre-adjustment to a constant relative humidity level, even if there is a fluctuation in the initial relative humidity. The setting of the constant relative humidity level can remove the necessity for the adjustment of the heating time in correspondence with each initial relative humidity.

Figure 5:
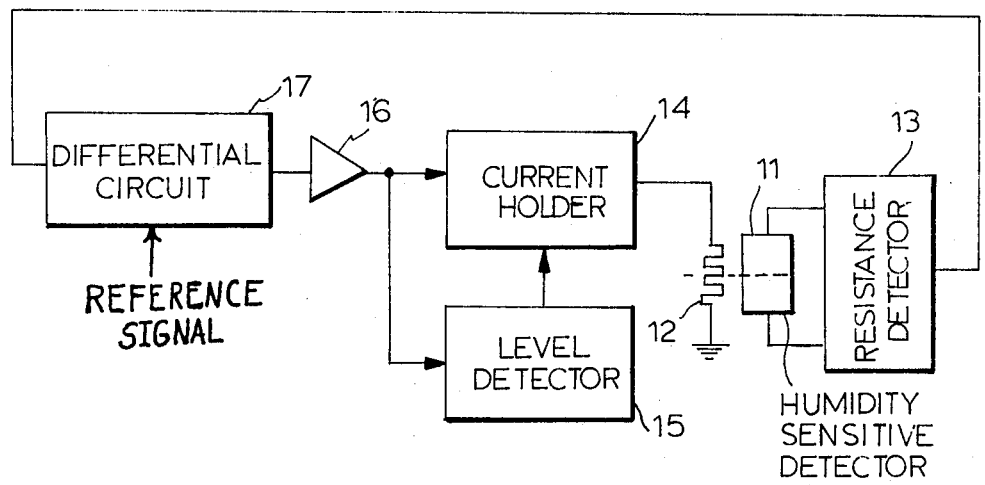
FIG. 5 is a block diagram of an example of a humidity sensitive resistor device according to this invention for achieving the operation shown in FIG. 4(b)

FIG. 5 shows the humidity sensitive resistor device according to this invention with a control circuit. Referring to FIG. 5, a resistance detector 13 is coupled to the humidity sensitive detector 11 and produces an electric signal corresponding to the resistance of the humidity sensitive resistor, which of course corresponds to the ambient humidity. The electric signal from the resistance detector 13 is applied to a differential circuit 17 to which a reference signal from a reference signal source (not shown but simply indicated by an arrow) is also applied. The reference signal is a signal which corresponds to a predetermined standard humidity. The differential circuit compares the two signals and produces a signal (which can be called a subtract signal) corresponding to the difference between the electric signal from the resistance detector and the reference signal. The subtract signal is applied to an amplifier 16 and then applied to a level detector 15 and a current holder 14. The level detector produces a control signal which corresponds to the subtract signal and which is applied to the current holder 14. The current holder 14 applies to the heater 12 an electric current corresponding to the subtract signal under the control of the control signal, whereby the humidity of the working surface of the humidity sensitive resistor is kept at the standard humidity level.

According to the controlling circuit, when the initial relative humidity in the oven is higher than the standard humidity, the heater is operated to lower the ambient relative humidity near the humidity sensitive resistor to the standard level.

Figure 6:
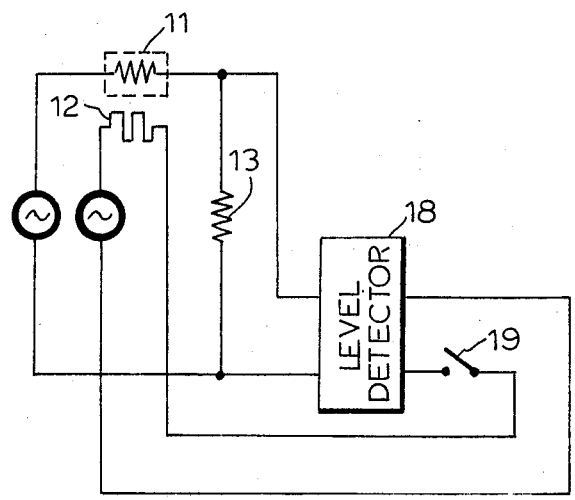
FIG. 6 is a block diagram of an example of a humidity sensitive resistor device according to this invention for stopping the current flowing through the heater by using the NTC thermistor property shown in FIG. 3.

FIG. 6 shows the humidity sensitive resistance device of this invention with another control circuit for heating the heater to a high temperature for cleaning (or removing) stains such as oil from the working surface of the humidity sensitive resistor. Of course, not only usual stains but also water drops which might have been deposited on the resistor surface can be removed thereby. Referring to FIG. 6, a resistor 13 which is a resistance detector is coupled to the humidity sensitive resistor 11 as shown and produces an electric signal corresponding to the resistance of the humidity sensitive resistor. The electric signal is a voltage across the resistor 13. This electric signal is applied to a level detector 18. When a switch 19 is switched on, an electric current flows through the heater 12, and the heater radiates radiant heat onto the humidity sensitive resistor 11. Thereby, the humidity sensitive resistor is heated up to a certain temperature.

Since the humidity sensitive resistor has an NTC thermistor region in a high temperature range as shown in FIG. 3, the resistance of the humidity sensitive resistor decreases as the temperature increases. Meanwhile, the level detector operates to detect the decrease of the resistance of the humidity sensitive resistor from a value above a predetermined value to a value below the predetermined value in the NTC thermistor region for cutting the current flowing through the heater to prevent excessive heating of the heater.

That is, when the resistance of the resistor 13 becomes lower than a predetermined value after the humidity sensitive resistor 11 is heated to a temperature outside the humidity sensing range (e.g. heated to 100° C), the level detector cuts the electric current flowing through the heater 12. The predetermined value corresponds to a temperature desired for cleaning the surface of the humidity sensitive resistor (i.e. removing stains from the resistor surface). Accordingly, by utilizing the NTC thermistor region of the humidity sensitive resistor, the heating of the heater 12 for removing stains such as oil can be carried out without danger of excessive heating thereof. Any suitable element or circuit can be used for the level detector. For example, a conventional relay can be used therefor. In the case of the above exemplary case, only about 20 seconds is necessary for heating the humidity sensitive resistor from 20° C to 400° C and cooling it back to 20° C.

As is apparent from the foregoing description, the provision of the heater arrangement in the basic structure of the humidity sensitive resistor device is very advantageous because the heater arrangement can be used to control the humidity sensing operation of the humidity sensitive resistor device as desired and to clean the surface of the humidity sensitive resistor. Especially, the presence of the NTC thermistor region of the humidity sensitive resistor can help the effective heating of the heater for the resistor surface cleaning.

The humidity sensitive resistor device according to this invention including or not including the control circuits described above can be used not only for cooking foods, but also for a variety of applications. And such humidity sensitive resistor device has a uniform and stable performance and can be mass produced at a low cost, as can be easily seen from the foregoing description.

What is claimed is:

1. A humidity sensitive resistor device for sensing the humidity of an ambient atmosphere, comprising: a humidity sensitive resistor having a metal oxide sintered substrate and electrodes on one surface thereof, the resistivity of said humidity sensitive resistor decreasing as the ambient humidity increases; and a heater positioned near said humidity sensitive resistor for applying radiant heat to said surface of said humidity sensitive resistor.

2. A humidity sensitive resistor device according to claim 1, wherein said metal oxide sintered substrate is made of a material taken from the group consisting of $Cr_2O_3$, $Fe_2O_3$, NiO, ZnO, $SnO_2$, $TiO_2$, $Al_2O_3$, MgO, $In_2O_3$, $MnO_2$, CuO, CoO, $MgCr_2O_4$, $FeCr_2O_4$, $NiCr_2O_4$, $MnCr_2O_4$, $CuCr_2O_4$, $CoCr_2O_4$, $Zn_2TiO_4$, $Zn_2SnO_4$, $Mg_2TiO_4$ and $Mg_2SnO_4$.

3. A humidity sensitive resistor device according to claim 2, wherein said metal oxide sintered substrate is made of $Cr_2O_3$.

4. A humidity sensitive resistor device according to claim 2, wherein said metal oxide sintered substrate is made of $MgCr_2O_4$.

5. A humidity sensitive resistor device according to claim 1, wherein each of said electrodes is made of a material taken from the group consisting of Ag, Au, Ag-Pd alloy, Ni-P alloy, Pt, $RuO_2$, NiO, $SnO_2$, $In_2O_3$, $TiO_2$, ZnO, $BaTiO_3$ and $BaPbO_3$.

6. A humidity sensitive resistor device according to claim 5, wherein each of said electrodes is made of a material taken from the group consisting of $RuO_2$, $SnO_2$ and $In_2O_3$.

7. A humidity sensitive resistor device according to claim 1, wherein said heater is a wire wound around and spaced from said humidity sensitive resistor.

8. A humidity sensitive resistor device according to claim 1, wherein said heater is made of a material taken from the group consisting of Ni-Cr alloy, Ni-Cr-Al alloy, Fe-Cr alloy, Ni-Al alloy and Pt.

9. A humidity sensitive resistor device according to claim 1, which further comprises: a resistance detector coupled to said humidity sensitive resistor for producing an electric signal corresponding to the resistance of said humidity sensitive resistor; a differential circuit coupled to said resistance detector and to a reference signal source for receiving from said differential circuit a reference signal corresponding to a predetermined standard humidity, the differential circuit producing a subtract signal corresponding to the difference between said electric signal from said resistance detector and said reference signal; a level detector coupled to said differential circuit for producing a control signal corresponding to said subtract signal; and a current holder coupled to said differential circuit and said level detector and said heater for applying to said heater an electric current corresponding to said subtract signal for keeping the humidity of said surface of said humidity sensitive resistor at said standard humidity.

10. A humidity sensitive resistor device according to claim 1, wherein said humidity sensitive resistor has an NTC thermistor region in a temperature range above the temperature range for humidity sensing operation, said humidity sensitive resistor device further comprising: a resistance detector coupled to said humidity sensitive resistor for producing an electric signal corresponding to the resistance of said humidity sensitive resistor; and a level detector coupled to said resistance detector for detecting the decrease of the resistance of said humidity sensitive resistor from a value above a predetermined value to a value below the predetermined value in said NTC thermistor region for cutting off the current through said heater to prevent excessive heating of said heater, said predetermined value corresponding to a temperature desired for cleaning said surface of said humidity sensitive resistor.

* * * * *